US008405714B2

(12) United States Patent
Matsushima et al.

(10) Patent No.: US 8,405,714 B2
(45) Date of Patent: Mar. 26, 2013

(54) PUPIL HIDDEN STATE DETECTING APPARATUS AND VEHICLE-MOUNTED CAMERA EMPLOYING THE SAME

(75) Inventors: Yukihiro Matsushima, Tokyo (JP); Sotaro Tsukizawa, Kanagawa (JP)

(73) Assignee: Panasonic Corporation, Osaka (JP)

( * ) Notice: Subject to any disclaimer, the term of this patent is extended or adjusted under 35 U.S.C. 154(b) by 35 days.

(21) Appl. No.: 13/171,524

(22) Filed: Jun. 29, 2011

(65) Prior Publication Data
US 2011/0298913 A1 Dec. 8, 2011

Related U.S. Application Data

(63) Continuation of application No. PCT/JP2010/005805, filed on Sep. 28, 2010.

(30) Foreign Application Priority Data

Jun. 3, 2010 (JP) .................................. 2010-127448

(51) Int. Cl.
*H04N 7/18* (2006.01)
(52) U.S. Cl. ........................................................ 348/78
(58) Field of Classification Search .................... None
See application file for complete search history.

(56) References Cited

U.S. PATENT DOCUMENTS

| 5,617,155 | A | 4/1997 | Ducarouge et al. | |
| 2003/0168317 | A1* | 9/2003 | Fromme et al. ............ | 198/502.1 |
| 2004/0151350 | A1 | 8/2004 | Tafuku et al. | |
| 2008/0253622 | A1* | 10/2008 | Tosa et al. ..................... | 382/117 |
| 2009/0231145 | A1* | 9/2009 | Wada et al. ................... | 340/575 |

FOREIGN PATENT DOCUMENTS

| JP | 2000-040148 A | 2/2000 |
| JP | 2004-234367 A | 8/2004 |
| JP | 3683613 B2 | 6/2005 |
| WO | 2008/007781 A1 | 1/2008 |

OTHER PUBLICATIONS

International Search Report for PCT/JP2010/005805.
Kenji Oka, et al., Development of a technique for estimating a driver's face pose and eye-gaze direction by a micro stereo camera in an automobile, Image Lab, vol. 21, No. 2, pp. 56-60, Feb. 2010.

\* cited by examiner

*Primary Examiner* — Sath V Perungavoor
*Assistant Examiner* — Kate Luo
(74) *Attorney, Agent, or Firm* — Pearne & Gordon LLP

(57) ABSTRACT

Provided is a pupil hidden state detecting apparatus which can detect directly a hidden state of a pupil without detecting a hiding object. The pupil hidden state detecting apparatus 20 is comprises: a visual line direction detecting section 22 operable to detect a direction of a visual line of a driver; a brightness gradient calculating section 23 operable to calculate a brightness gradient of an image of an eye area; a gradient intensity calculating section 24 operable to calculate a gradient intensity vertical distribution; a gradient intensity storing section 25 adapted to store therein the data of a reference gradient intensity vertical distribution under the state that the direction of the visual line of the driver is toward an instrument panel; a difference calculating section 26 operable to calculate a difference between the gradient intensity vertical distribution of the current frame and the reference gradient intensity vertical distribution; an evaluation value calculating section 27 operable to calculate an evaluation value indicating a degree of possibility that the pupil of the driver is hidden; and a pupil hidden judging section 29 operable to judge that the pupil is hidden, when the evaluation values indicative of the pupil being hidden is continued.

3 Claims, 2 Drawing Sheets

(a)  DETECTING AN EYE REGION (b)  CALCULATING BRIGHTNESS GRADIENT OF RESPECTIVE PIXELS OF THE EYE REGION (c)  CALCULATING A SUM OF INTENSITY OF THE BRIGHTNESS GRADIENT WITH RESPECT TO EACH Y-COORDINATE

PUPIL HIDDEN STATE DETECTING APPARATUS AND VEHICLE-MOUNTED CAMERA EMPLOYING THE SAME

CROSS REFERENCE

This application claims the benefit of Patent Application No. 2010-127448, filed in Japan on Jun. 3, 2010, the content of which is incorporated herein by reference.

TECHNICAL FIELD

The present invention relates to a pupil hidden state detecting apparatus used for a device to detect states of a vehicle's driver such as a drowsy driving state and an inattentive driving state, and a vehicle-mounted camera employing the same.

BACKGROUND ART

The device for detecting the states of the vehicle's driver such as the drowsy driving state and the inattentive driving state is needed to detect a pupil of the driver from a taken image of the driver. However, in case that the driver wears glasses, the pupil may be hidden behind a frame of the glasses. In this case, the device can not correctly detect the pupil of the driver, thereby resulting in the fact that the device is needed to obtain information indicating whether the pupil is hidden or not. One of the methods to obtain the information is known as including steps of detecting the frame of the glasses, and detecting whether the pupil is hidden behind the detected frame (see, for example, Patent Document 1).

CITATION LIST

Patent Literature

[PTL 1]
Patent Literature 1: Japanese Patent No. 3683613

SUMMARY OF INVENTION

Technical Problem

The method disclosed in the Patent Literature 1 is needed to detect an outline of the frame of the glasses. The method, however, encounters such a problem that the frame of the glasses is difficult to be detected, because of the fact that there have so far been a wide variety of forms of the frames of the glasses.

At the time of taking the image of the driver, the pupil is hidden behind not only the frame of the glasses but also a bottom lid, a mask, a hair, and so on. Therefore, a technology capable of detecting directly a hidden state of the pupil without detecting a hiding object is required.

It is, therefore, a subject of the present invention to provide a pupil hidden state detecting apparatus which can detect directly the hidden state of the pupil without detecting the hiding object, and a vehicle-mounted camera employing the same.

Solution to Problem

According to first aspect of the present invention, there is provided a drive assist display apparatus comprising: an imaging section located in an area where a driver of a vehicle is capable of watching directly under the state that the driver directs a visual line toward an instrument panel of the vehicle so as to take an image of a face of the driver to output data of a face image at predetermined frame intervals; an eye region detecting section operable to detect an eye region of the driver from the face image; a visual line direction detecting section operable to detect a visual line direction of the driver from the image of the eye region; a brightness gradient calculating section operable to calculate a brightness gradient of each pixel constituting the image of the eye region; a gradient intensity calculating section operable to calculate a sum of intensity of the brightness gradients calculated by the brightness gradient calculating section with respect to each vertical coordinate of the image of the eye region so as to calculate data of a vertical distribution of the intensity of the gradient with respect to each frame; a gradient intensity storing section adapted to store therein the data of the vertical distribution of the intensity of the gradient calculated by the gradient intensity calculating section, when the visual line direction detected by the visual line direction detecting section is toward the instrument panel of the vehicle; a difference calculating section operable to calculate a difference between the vertical distribution of the intensity of the gradient stored in the gradient intensity storing section and the vertical distribution of the intensity of the gradient of a current frame; and a pupil hidden judging section operable to judge whether a pupil is hidden or not on the basis of the difference calculated by the difference calculating section.

In accordance with the above construction, the drive assist display apparatus according to the present invention is designed to judge whether a pupil is hidden or not on the basis of the vertical distribution of the intensity of the gradient in the image of the eye region under the state that the driver watches the instrument panel, in other words, the state that the eye of the driver is not hidden. The drive assist display apparatus can therefore detect directly the hidden state of the pupil without detecting the hiding object.

The drive assist display apparatus may further comprises an evaluation value calculating section operable to calculate an evaluation value indicating a degree of possibility that the pupil of the driver is hidden with respect to each frame, wherein the pupil hidden judging section is operable to judge that the pupil is hidden, when the number of contiguous frames with the evaluation values indicative of the pupil being hidden is larger or equal to the predetermined threshold number of frames.

In accordance with the above construction, the drive assist display apparatus according to the present invention is designed to judge whether a pupil is hidden or not on the basis of the evaluation value indicating a degree of possibility that the pupil of the driver is hidden. The drive assist display apparatus can therefore detect directly the hidden state of the pupil without detecting the hiding object.

According to second aspect of the present invention, there is provided a vehicle-mounted camera comprising: a pupil hidden state detecting apparatus as set forth in claim 1 or 2; and an imaging apparatus having an imaging section located in an area where a driver of a vehicle is capable of watching directly under the state that the driver directs a visual line toward an instrument panel of the vehicle so as to take an image of a face of the driver to output data of a face image at predetermined frame intervals.

In accordance with the above construction, the vehicle-mounted camera can detect directly the hidden state of the pupil without detecting the hiding object.

Advantageous Effects of Invention

The present invention provides a drive assist display apparatus which can detect directly the hidden state of the pupil without detecting the hiding object, and a vehicle-mounted camera employing the same.

DESCRIPTION OF EMBODIMENT

The embodiment of the present invention will be described hereinafter with reference to the drawings.

The construction of a vehicle-mounted camera according to the embodiment of the present invention will be described hereinafter with reference to FIGS. 1 and 2.

Figure 1:
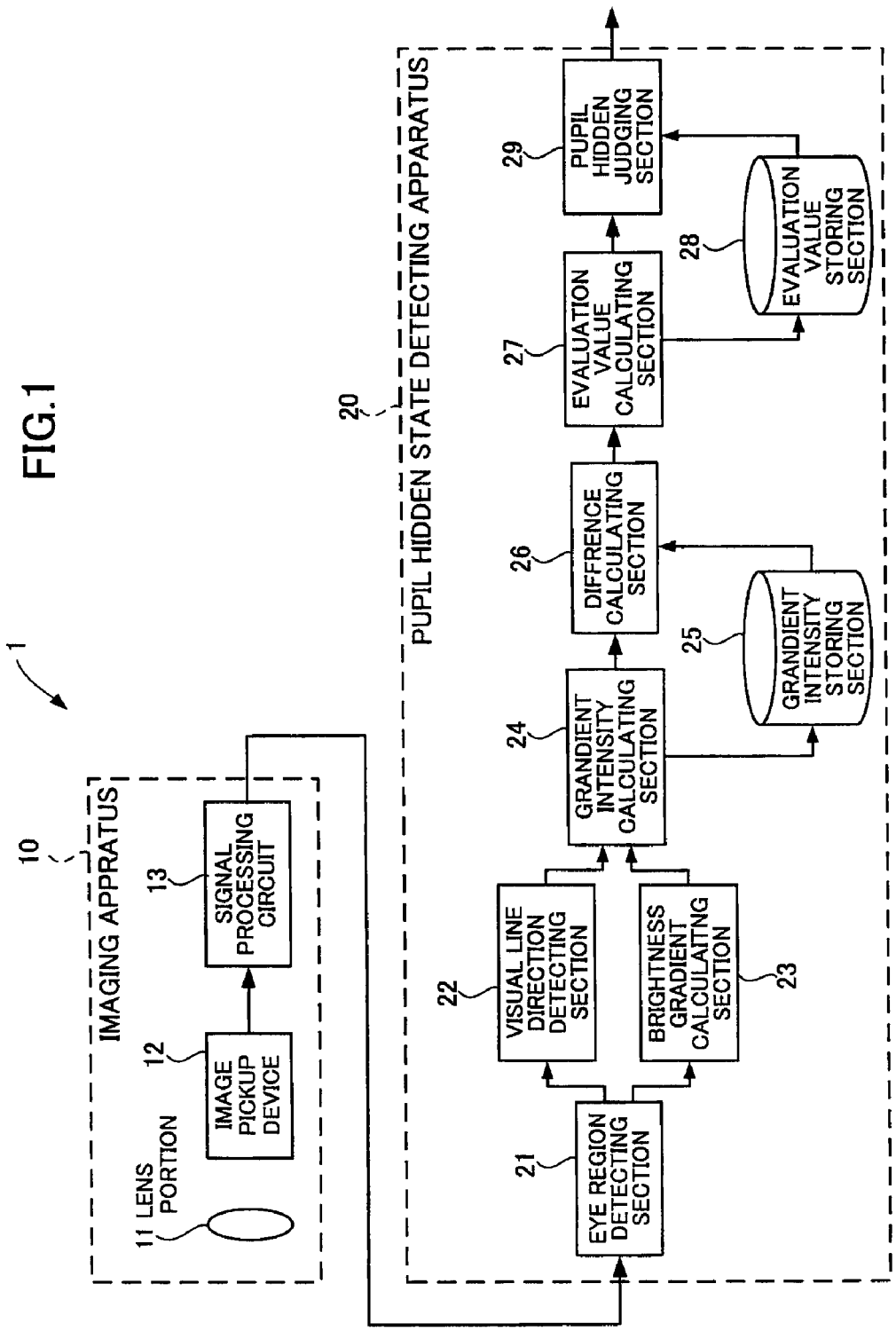
FIG. 1 is a block diagram showing a vehicle-mounted camera according to an embodiment of the present invention.
Figure 2:
FIG. 2 is a conceptual diagram showing a detected image of an eye region, and ways of calculating a distribution of a brightness gradient and a vertical distribution of an intensity of the gradient.
Figure 2:
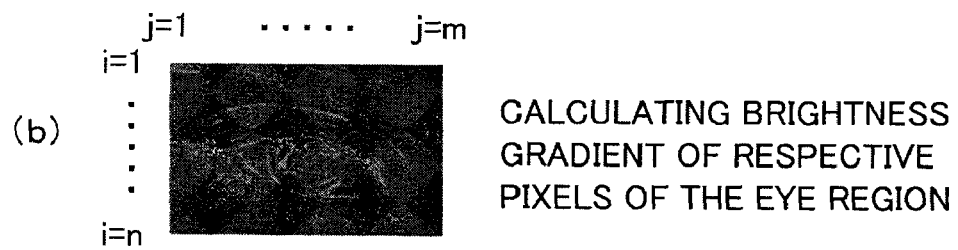
Figure 2:
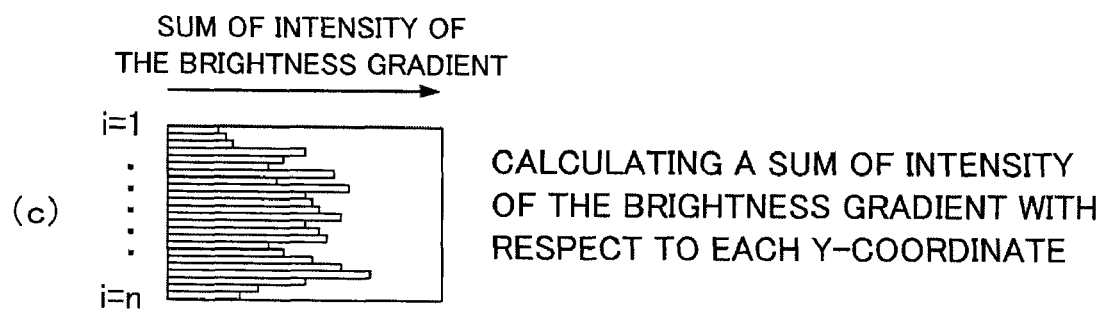

As shown in FIG. 1, the vehicle-mounted camera 1 according to the embodiment comprises an imaging apparatus 10 and a pupil hidden state detecting apparatus 20.

The imaging apparatus 10 comprises a lens portion 11, an image pickup device 12 as an imaging section, and a signal processing circuit 13. The imaging apparatus 10 is designed to taken an image of a face of a driver of a vehicle to output image data of the taken image at predetermined frame intervals.

The imaging apparatus 10 is located in an area where the driver is capable of watching directly under the state that the driver directs a visual line at an instrument panel. For example, the imaging apparatus 10 is located inside the instrument panel of the vehicle. The instrument panel has a speedometer, a tachometer, a fuel level indicator, a water temperature meter, a trochometer, and other indicators indicating information needed for traveling the vehicle. The imaging apparatus 10 is, for example, located between the speedometer and the tachometer. By the construction, the imaging apparatus 10 can image directly a pupil of the driver under the state that the driver directs a visual line toward the instrument panel.

While there has been described about the fact that the imaging apparatus 10 is located inside the instrument panel, the imaging apparatus 10 is not limited to be located inside the instrument panel according to the present invention. For example, the imaging apparatus 10 may be located inside the instrument panel may be located on a steering column accommodating therein a steering shaft so as to image directly the pupil.

The lens portion 11 is adapted to focus light onto an imaging area of the image pickup device 12 to provide an image of a subject. The image pickup device 12 is adapted to create a subject image on the basis of the image of the subject provided by the lens portion 11. The image pickup device 12 is constituted by a CCD (Charge Coupled Device). The image pickup device 12 may be constituted by a MOS (Metal Oxide Semiconductor) image pickup device.

The signal processing circuit 13 is constituted by a correlated double sampling circuit, an automatic gain control circuit and an AD converter and so on, and adapted to output the subject image. The correlated double sampling circuit is operable to remove noises from the subject image created by the image pickup device 12. The automatic gain control circuit is operable to control automatically a gain of a signal from the correlated double sampling circuit. The AD converter is operable to convert an analog signal from the automatic gain control circuit into a digital signal.

The pupil hidden state detecting apparatus 20 is comprises an eye region detecting section 21, a visual line direction detecting section 22, a brightness gradient calculating section 23, a gradient intensity calculating section 24, a gradient intensity storing section 25, a difference calculating section 26, an evaluation value calculating section 27, an evaluation value storing section 28 and a pupil hidden judging section 29.

The eye region detecting section 21 is operable to detect an eye region of the driver from a face image with respect to each frame to output image data of the eye region to the visual line direction detecting section 22 and the brightness gradient calculating section 23. The image of the eye region detected by the eye region detecting section 21 is shown in FIG. 2(a) as an example. The image of the eye region shown in FIG. 2(a) is taken under the state that the driver watches the instrument panel.

The visual line direction detecting section 22 has image data of the eye region inputted therein from the eye region detecting section 21. The visual line direction detecting section 22 is operable to detect an image of a pupil from the image of the eye region to detect a direction of a visual line with respect to each frame. The visual line direction detecting section 22 is adapted to output data indicating the detected direction of the visual line of the driver to the gradient intensity calculating section 24.

The brightness gradient calculating section 23 has image data of the eye region inputted therein from the eye region detecting section 21. The brightness gradient calculating section is operable to calculate a brightness gradient of the image of the eye region with respect to each frame. The calculation of the brightness gradient will be concretely described hereinafter with reference to FIG. 2(b). As shown in FIG. 2(b), the image of the eye region detected by the eye region detecting section 21 is constituted by a plurality of pixels. The number of pixels is assumed to have n pixels in a vertical direction (in the direction of a y-axis) each from i=1 to i=n, and m pixels in a horizontal direction (in the direction of an x-axis) each from j=1 to j=m. In this case, the brightness gradient calculating section 23 is operable to calculate brightness gradients of respective n×m pixels.

The gradient intensity calculating section 24 is operable to calculate a sum of intensity (absolute value) with respect to each vertical coordinate of each frame. The calculated sum with respect to each vertical coordinate is hereinafter referred to as "gradient intensity vertical distribution". The gradient intensity vertical distribution is shown in FIG. 2(c) as an example. As shown in FIG. 2(c), The gradient intensity calculating section 24 is operable to calculate the gradient intensity vertical distribution by calculating the sum of intensity of the brightness gradients with respect to each y-coordinate from a column i=1 to a column i=n.

The gradient intensity calculating section 24 is operable to store the gradient intensity vertical distribution into the gradient intensity storing section 25 under the state that the direction of the visual line of the driver detected by the visual line direction detecting section 22 is toward the instrument panel. In this case the gradient intensity vertical distribution is hereinafter referred to as "reference gradient intensity vertical distribution". In other words, the gradient intensity storing section 25 is adapted to store therein the gradient intensity vertical distribution of the eye region as the reference gradient intensity vertical distribution under the state that the pupil is not hidden.

The difference calculating section 26 has inputted therein data indicating the gradient intensity vertical distribution of a current frame calculated by the gradient intensity calculating section 24. The difference calculating section 26 is operable to read out the data indicating the reference gradient intensity vertical distribution from the gradient intensity storing section 25. The difference calculating section 26 is operable to calculate a difference between the gradient intensity vertical distribution of the current frame and the reference gradient intensity vertical distribution.

The evaluation value calculating section 27 has inputted therein data indicating the difference calculated by the difference calculating section 26. The evaluation value calculating section 27 is operable to calculate an evaluation value indicating a degree of possibility that the pupil is hidden with respect to each frame. The evaluation value calculating section 27 is operable to calculate the evaluation value E by a following formula.

$$E = \Sigma |B(i) - A(i)|$$

The A(i) is indicates the sum of intensity of the brightness gradients with respect to i on the y-coordinate in the reference gradient intensity vertical distribution. The B(i) is indicates the sum of intensity of the brightness gradients with respect to i on the y-coordinate in the gradient intensity vertical distribution of the current frame. The evaluation value E is calculated by the $\Sigma$ operator for obtaining an integrated value from i=1 to i=n. The evaluation value calculating section 27 is operable to store data indicating the calculated evaluation value into the evaluation value storing section 28.

The pupil hidden judging section 29 has inputted therein the data indicating the evaluation value of the current frame calculated by the evaluation value calculating section 27. The pupil hidden judging section 29 is operable to read out the evaluation value of a previous frame such as, for example, a 1-frame before the current frame. The pupil hidden judging section 29 is operable to compare the data indicating the evaluation value of the current frame with the data indicating the 1-frame before the current frame. The pupil hidden judging section 29 is operable to judge that the pupil is hidden and operable to output a signal indicating of the pupil being hidden, when the number of contiguous frames with the evaluation values indicative of the pupil being hidden is larger or equal to the predetermined threshold number of frames.

The operation of a vehicle-mounted camera according to the embodiment of the present invention will be described hereinafter.

The imaging apparatus 10 firstly takes an image of the face of the driver of the vehicle, and output data of the face image at predetermined frame intervals. In detail, the lens portion 11 focuses light onto the imaging area of the image pickup device 12 to provide the image of the subject. The image pickup device 12 creates the subject image on the basis of the image of the subject provided by the lens portion 11. The signal processing circuit 13 performs predetermined signal processing, and output the digital signal indicating the data of the face image.

In the pupil hidden state detecting apparatus 20, the eye region detecting section 21 then detects the image of the eye region of the driver from the face image taken by the imaging apparatus 10 with respect to each frame, and outputs the image data of the eye region to the visual line direction detecting section 22 and the brightness gradient calculating section 23.

The visual line direction detecting section 22 inputs therein the image data, and then detects the direction of the visual line of the driver with respect to each frame by detecting the image of the pupil from the image of eye region. The visual line direction detecting section 22 then output the data indicating the detected direction of the visual line of the driver to the gradient intensity calculating section 24.

The brightness gradient calculating section 23 inputs therein the image data of the eye region from the eye region detecting section 21, and then calculates the brightness gradient of the image of the eye region.

The gradient intensity calculating section 24 then calculates the gradient intensity vertical distribution with respect to each vertical coordinate of each frame. The gradient intensity calculating section 24 then stores the gradient intensity vertical distribution as the reference gradient intensity vertical distribution into the gradient intensity storing section 25, when the direction of the visual line of the driver detected by the visual line direction detecting section 22 is toward the instrument panel. On the other hand, the gradient intensity calculating section 24 does not stores any data until the direction of the visual line of the driver is toward the instrument panel from starting of detecting the direction of the visual line of the driver by the visual line direction detecting section 22.

The difference calculating section 26 inputs therein the data of the gradient intensity vertical distribution of the current frame. The difference calculating section 26 then reads out the data indicating the reference gradient intensity vertical distribution from the gradient intensity storing section 25. The difference calculating section 26 then calculate the difference between the gradient intensity vertical distribution of the current frame and the reference gradient intensity vertical distribution.

The evaluation value calculating section 27 inputs therein the data indicating the difference calculated by the difference calculating section 26. The evaluation value calculating section 27 then calculates the evaluation value indicating a degree of possibility that the pupil is hidden with respect to each frame, and stores the data indicating the calculated evaluation value into the evaluation value storing section 28.

The pupil hidden judging section 29 inputs therein the data indicating the evaluation value of the current frame calculated by the evaluation value calculating section 27. The pupil hidden judging section 29 then reads out the evaluation value of the 1-frame before the current frame. The pupil hidden judging section 29 then compares the data indicating the evaluation value of the current frame with the data indicating the 1-frame before the current frame. The pupil hidden judging section 29 then judges that the pupil is hidden and outputs a signal indicating of the pupil being hidden, when the number of contiguous frames with the evaluation values indicative of the pupil being hidden is larger or equal to the predetermined threshold number of frames.

As will be seen from the foregoing description, it is to be understood that the drive assist display apparatus 20 according to the present invention is designed to judge whether the pupil is hidden or not on the basis of the vertical distribution of the intensity of the gradient in the image of the eye region under the state that the driver watches the instrument panel, in other words, the state that the eye of the driver is not hidden. The drive assist display apparatus can therefore detect directly the hidden state of the pupil without detecting the hiding object.

This leads in the fact that the drive assist display apparatus 20 according to the present invention can detect the hidden state of the pupil by the frame of the glasses of the driver and other incidents, thereby improving a detecting accuracy of the pupil hidden state.

There has been described in the foregoing embodiment about the fact that the pupil hidden judging section 29 is operable to judge whether the pupil is hidden or not on the basis of the evaluation value indicating the degree of possibility that the pupil of the driver is hidden, but the pupil hidden judging section 29 is not limited to the description. For example, when the difference calculated by the difference calculating section 26 is larger than a predetermined threshold, the pupil hidden judging section 29 may be operable to judge that the pupil is hidden.

INDUSTRIAL APPLICABILITY

As described above, the pupil hidden state detecting apparatus and the vehicle-mounted camera employing the same each has an effect of detecting directly the hidden state of the pupil without detecting the hiding object, and available for the device to detect states of the vehicle's driver such as the drowsy driving state and the inattentive driving state.

REFERENCE SIGNS LIST 1 vehicle-mounted camera
10 imaging apparatus
11 lens portion
12 image pickup device (imaging section)
13 signal processing circuit
20 pupil hidden state detecting apparatus
21 eye region detecting section
22 visual line direction detecting section
23 brightness gradient calculating section
24 gradient intensity calculating section
25 gradient intensity storing section
26 difference calculating section
27 evaluation value calculating section
28 evaluation value storing section
29 pupil hidden judging section

What is claimed is:

1. A pupil hidden state detecting apparatus comprising:
    an imaging section located in an area where a driver of a vehicle is capable of watching directly under the state that the driver directs a visual line toward an instrument panel of the vehicle so as to take an image of a face of the driver to output data of a face image at predetermined frame intervals;
    an eye region detecting section operable to detect an eye region of the driver from the face image;
    a visual line direction detecting section operable to detect a visual line direction of the driver from the image of the eye region;
    a brightness gradient calculating section operable to calculate a brightness gradient of each pixel constituting the image of the eye region;
    a gradient intensity calculating section operable to calculate a sum of intensity of the brightness gradients calculated by the brightness gradient calculating section with respect to each vertical coordinate of the image of the eye region so as to calculate data of a vertical distribution of the intensity of the gradient with respect to each frame;
    a gradient intensity storing section adapted to store therein the vertical distribution of the intensity of the gradient calculated by the gradient intensity calculating section as a reference gradient intensity vertical distribution, when the visual line direction detected by the visual line direction detecting section is toward the instrument panel of the vehicle;
    a difference calculating section operable to calculate a difference between the stored reference gradient intensity vertical distribution in the gradient intensity storing section and the vertical distribution of the intensity of the gradient of a current frame; and
    a pupil hidden judging section operable to judge whether a pupil is hidden or not on the basis of the difference calculated by the difference calculating section.

2. The pupil hidden state detecting apparatus as set forth in claim 1, further comprising
    an evaluation value calculating section operable to calculate an evaluation value indicating a degree of possibility that the pupil of the driver is hidden with respect to each frame, wherein
    the pupil hidden judging section is operable to judge that the pupil is hidden, when the number of contiguous frames with the evaluation values indicative of the pupil being hidden is larger or equal to the predetermined threshold number of frames.

3. A vehicle-mounted camera comprising:
    a pupil hidden state detecting apparatus as set forth in claim 1 or 2; and
    an imaging apparatus having an imaging section located in an area where a driver of a vehicle is capable of watching directly under the state that the driver directs a visual line toward an instrument panel of the vehicle so as to take an image of a face of the driver to output data of a face image at predetermined frame intervals.

* * * * *